United States Patent [19]
Wynkoop et al.

[11] Patent Number: 5,292,306
[45] Date of Patent: Mar. 8, 1994

[54] METHOD OF DETECTING OCCLUSIONS IN A SOLUTION PUMPING SYSTEM

[75] Inventors: Richard D. Wynkoop, Des Plaines; John E. Ogden; Sheldon M. Wecker, both of Libertyville, all of Ill.

[73] Assignee: Abbott Laboratories, Abbott Park, Ill.

[21] Appl. No.: 11,062

[22] Filed: Jan. 29, 1993

[51] Int. Cl.$^5$ .............................................. A61M 1/00
[52] U.S. Cl. ...................................... 604/51; 604/152; 417/53; 417/63
[58] Field of Search ................ 604/49, 51, 131, 151, 604/152; 417/53, 63

[56] References Cited

U.S. PATENT DOCUMENTS

| | | | |
|---|---|---|---|
| 4,322,201 | 3/1982 | Archibald | 604/152 |
| 4,669,960 | 6/1987 | Allen et al. | 417/63 |
| 4,720,675 | 10/1987 | Aldrovandi et al. | 417/63 |
| 4,784,577 | 11/1988 | Ritson et al. | 417/63 |
| 4,836,752 | 6/1989 | Burkett | 417/63 |
| 5,103,211 | 4/1992 | Daoud et al. | 417/63 |
| 5,116,203 | 5/1992 | Natwick et al. | 417/63 |

Primary Examiner—John G. Weiss
Attorney, Agent, or Firm—A. Nicholas Trausch

[57] ABSTRACT

A method of detecting occlusions in a solution pumping system includes monitoring and analyzing pressures within the system during selected portions of a pumping cycle. The pumping system of the illustrated embodiment includes a positive displacement pump operated by a reciprocable pump piston, with analysis of pressures within the system identifying those conditions which reflect the presence of an occlusion either upstream or downstream of the positive displacement pump. A suitable signal or alarm can then be activated to alert operating personnel.

12 Claims, 4 Drawing Sheets

METHOD OF DETECTING OCCLUSIONS IN A SOLUTION PUMPING SYSTEM

TECHNICAL FIELD

The present invention generally relates to a solution pumping system which can be advantageously employed for preparation of patient parenteral solutions, and more particularly a method of detecting occlusions in the pumping system by monitoring fluid pressures in the system.

BACKGROUND OF THE INVENTION

Healthcare facilities require preparation and administration of very large numbers of parenteral solutions for patients. Such solutions are administered for both nutritional and therapeutic purposes, and thus efficient liquid-handling systems are required for cost-effective preparation of such solutions, and their administration to patients.

To this end, positive displacement fluid pumping devices have been developed for both preparation and administration of parenteral solutions. Such devices permit precise control during pumping of solutions, thus facilitating solution administration and preparation.

U.S. Pat. Nos. 4,639,245, to Pastrone et al., 4,818,186, to Pastrone et al., and 4,842,584, to Pastrone, all of which are hereby incorporated by reference, disclose a positive displacement fluid infusion pumping device and components thereof, which have met with widespread acceptance by the healthcare industry. This pumping system includes a combination of a pump driver and an associated removable and disposable pump cassette. The pump cassette includes a self-contained positive displacement pump device, which is operated by a reciprocable pump plunger or piston of the associated pump driver. The pump driver includes selectively operable valve actuators, which cooperate with valve mechanisms provided in the pump cassette for accurate and highly automated administration and infusion of parenteral solutions.

Commonly-assigned U.S. patent application Ser. No. 07/444,459, filed Dec. 1, 1989, now U.S. Pat. No. 5,062,774, discloses a solution pumping system generally of the above type, including a disposable pump cassette, and an associated pump driver. The system of this application is particularly configured for automatic compounding and preparation of parenteral solutions, for subsequent infusion to a patient. This application is hereby incorporated by reference.

Solution pumping systems of the above type employ preassembled, disposable pump cassettes. Typically, such pump cassettes include a cassette body having juxtaposed front and rear body members, between which is positioned a membrane-like elastomeric diaphragm. The diaphragm cooperates with the front body member to provide valve mechanisms at various inlets and outlets defined by the front body member, with openings in the rear body member exposing the diaphragm for operation of the valve mechanisms by valve actuators of the associated pump driver.

Additionally, the front body member of the cassette defines a pump chamber, which, together with the internal diaphragm, provides the self-contained positive displacement pump of the cassette. The rear body member defines an opening through which a reciprocable pump piston of the associated driver is movable for operating the cassette, whereby liquid can be pumped through the cassette.

During the use of the above type of pumping systems for preparation or administration of parenteral solutions, various tubing sets, containers, clamp mechanisms and the like, are employed for handling and controlling liquid flow. Proper operation of the system requires that liquid is able to flow throughout the various tubing sets, in and out of the various containers, and through the pump cassette itself. Kinking or excessive bending of the tubing material can restrict fluid flow, thus detracting from efficient and accurate operation of the system. Similarly, inadvertent blockage of a container, a container vent, or flow path of the pump cassette can result in improper system operation.

The present invention contemplates a method of operating a solution pumping system which facilitates monitoring occlusions or blockages in the system, with suitable alarms or like devices provided to alert operating personnel of a system occlusion.

SUMMARY OF THE INVENTION

The present invention relates to a method of operating a solution pumping system which, in the illustrated embodiment, includes a positive displacement pump operated by a reciprocable pump piston. In order to detect any occlusions or blockages which may exist in the system, fluid pressures within the system are monitored and analyzed, with such analysis identifying those conditions which reflect the presence of an occlusion either downstream or upstream of the positive displacement pump of the system. A suitable signal or alarm can then be activated to alert operating personnel.

In accordance with the illustrated embodiment, a solution pumping system which is particularly suitable for preparation of parenteral solutions, includes a pump cassette having a positive displacement pump. The pump cassette is used in operative association with a pump driver of the system, with the driver including a reciprocable pump piston. Reciprocation of the pump piston acts on the pump cassette to create a positive liquid pressure at the pump during a pumping stroke, and a negative liquid pressure during a return stroke. Operation of associated valve mechanisms, in coordination with stroking of the pump piston, controls liquid flow into and out of the pump.

As noted, occlusions in the system are detected by monitoring and analyzing pressures within the system during operation. While many different pressure analysis techniques can be employed to detect the existence of an occlusion or other blockage in the system, the present disclosure contemplates a desirably straightforward, highly reliable and consistent analysis method, as follows.

To detect occlusion downstream of the positive displacement pump, the system is operated to measure an initial pressure, $P_I$, prior to operation of the pump, and after opening of an outlet valve through which liquid from the pump of the system is pumped. As the system is operated to pump liquid by advancing the pump piston, a measurement is taken of the peak pressure, $P_P$, at the pump during the pumping stroke. Thereafter, a pressure $P_1$, corresponding to the peak pressure of the system, is determined by subtracting $P_I$ from $P_P$.

At this point in operation, the pressure $P_1$ is compared to a predetermined value, $P_{OCC}$, to provide an initial indication of downstream occlusion. In the event that $P_1$ exceeds $P_{OCC}$, the system operates to provide a signal indicating occlusion of the system downstream of the pump.

If no downstream occlusion is detected at this stage, the system next compares the pressure $P_1$ to a predetermined value $P_{REF}$. $P_{REF}$ corresponds to a value selected to distinguish a viscous solution from a non-viscous solution. Because pumping of a viscous solution generally creates higher pressures within the system, thereby requiring longer time periods for stabilization of system pressures, this step of the present method dictates the manner in which the next step of occlusion detection is performed.

Specifically, after comparison of $P_1$ to $P_{REF}$, the operation includes waiting one of: (1) a first predetermined time interval $T_{A(1)}$ after determining if pressure $P_1$ is less than $P_{REF}$, indicating a relatively non-viscous liquid, and (2) a second predetermined time interval $T_{A(2)}$, greater than $T_{A(1)}$, if the pressure $P_1$ is greater than $P_{REF}$, indicating a relatively viscous liquid.

In actual practice, a time delay or waiting period of 0.345 seconds is used for the value $T_{A(1)}$, while a relatively longer time period, on the order of 1.0 seconds, is used for the time interval $T_{A(2)}$.

The system is next operated to determine a pressure $P_2$ corresponding to the pressure of the system at the conclusion of the designated time interval. $P_2$ is determined by measuring the pressure $P_{SYS}$ of the system at that time, and subtracting therefrom the value of the initial pressure $P_I$ of the system.

Finally, a signal is provided indicating occlusion of the system downstream of the pump if $P_2$ exceeds a predetermined value. As will be appreciated, such a signal will be provided in the event of a partial system blockage which may have been insufficient to trigger the earlier, initial downstream occlusion detection step.

Occlusions upstream of the system pump are detected in a similar manner. After waiting the above-noted time interval $T_{A(1,2)}$, the outlet valve is closed, so there is not a fluid path from the pump chamber of the pump (which path is open from the pump during filling of a container with parenteral solution with the illustrated system). Thereafter, an inlet valve to the pump is opened so there is a fluid path from a so-called source container (holding one of the solutions of other liquids being compounded with the system) to the pump chamber of the system pump. A pressure, $P_R$, is measured, which is the head height of the source container.

It is next established when completion of one of the return strokes of the pump has been effected (which can be easily determined by monitoring operation of the drive for the pump piston), and thereafter waiting a predetermined time interval $T_B$. Again, waiting such a time interval facilitates stabilization of pressures within the system.

Next, a pressure $P_3$, corresponding to the pressure of the system is determined. Thereafter, the value of $P_3$ is compared to $P_R$, with a signal provided indicating occlusion of the system upstream of the pump if the difference between $P_R$ and $P_3$ is greater than or equal to a predetermined value.

Other features and advantages of the present invention will become readily apparent from the following detailed description, the accompanying drawings, and the appended claims.

DETAILED DESCRIPTION

Figure 1:
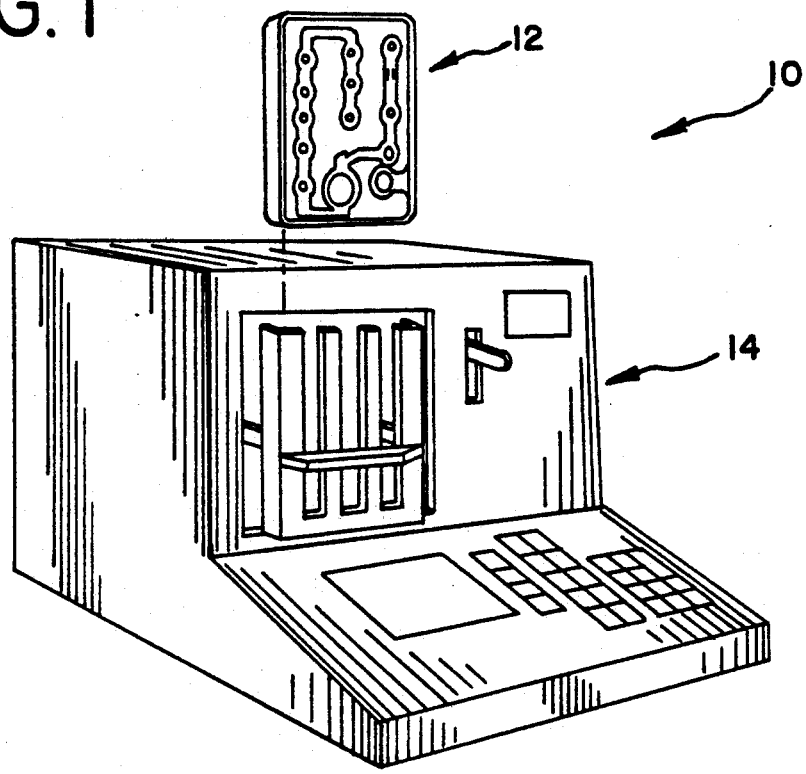
FIG. 1 is a perspective view of a solution pumping system, including a pump driver and a disposable pump cassette, which is operable in accordance with the principles of the present invention.

While the present invention is susceptible of embodiment in various forms, there is shown in the drawings and will hereinafter be described a presently preferred embodiment, with the understanding that the present disclosure is to be considered as an exemplification of the invention, and is not intended to limit the invention to the specific embodiment illustrated.

For purposes of disclosing the present invention, operation of an exemplary solution pumping system will be discussed in detail. As will be appreciated, the controls of the system are preferably programmable to perform the sequence of steps of the present invention in an automated fashion. Efficient, predictable, and reliable operation of the pumping system is achieved in this manner.

With reference now to the drawings, therein is illustrated a solution pumping system 10 operable in accordance with the principles of the present invention. The illustrated system is shown in the form of a so-called solution compounder, that is, a system particularly suited for compounding and preparation of parenteral solutions for subsequent administration to patients. However, it will be appreciated that a system operable in accordance with the principles disclosed herein can be readily configured for infusion of such solutions, or for other applications.

The solution pumping system includes a disposable pump cassette 12 which is removably positionable in operative association with a pump driver 14. For use in compounding parenteral solutions, the system is joined, via appropriate tubing sets, with containers of solutions to be compounded, and with a container into which appropriate quantities of the various solutions are mixed. The resultant admixture is thus ready for patient administration. Because this type of system is capable of efficiently and accurately preparing very large numbers of such admixtures, the system would ordinarily be used in the pharmacy of a healthcare facility, preferably within a laminar-flow hood.

Figure 2:
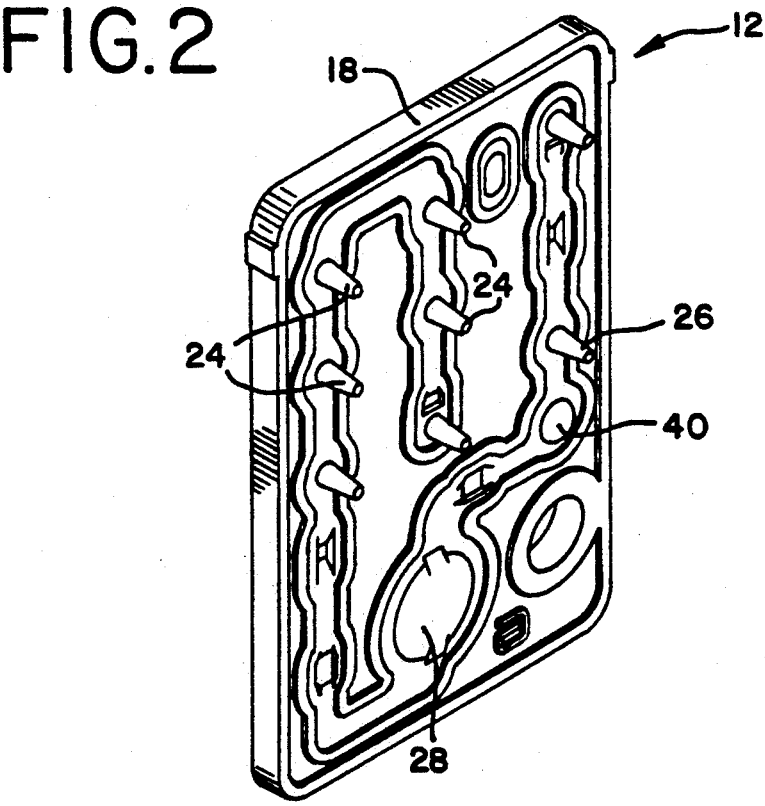
FIG. 2 is a perspective view of the pump cassette illustrated in FIG. 1.
Figure 3:
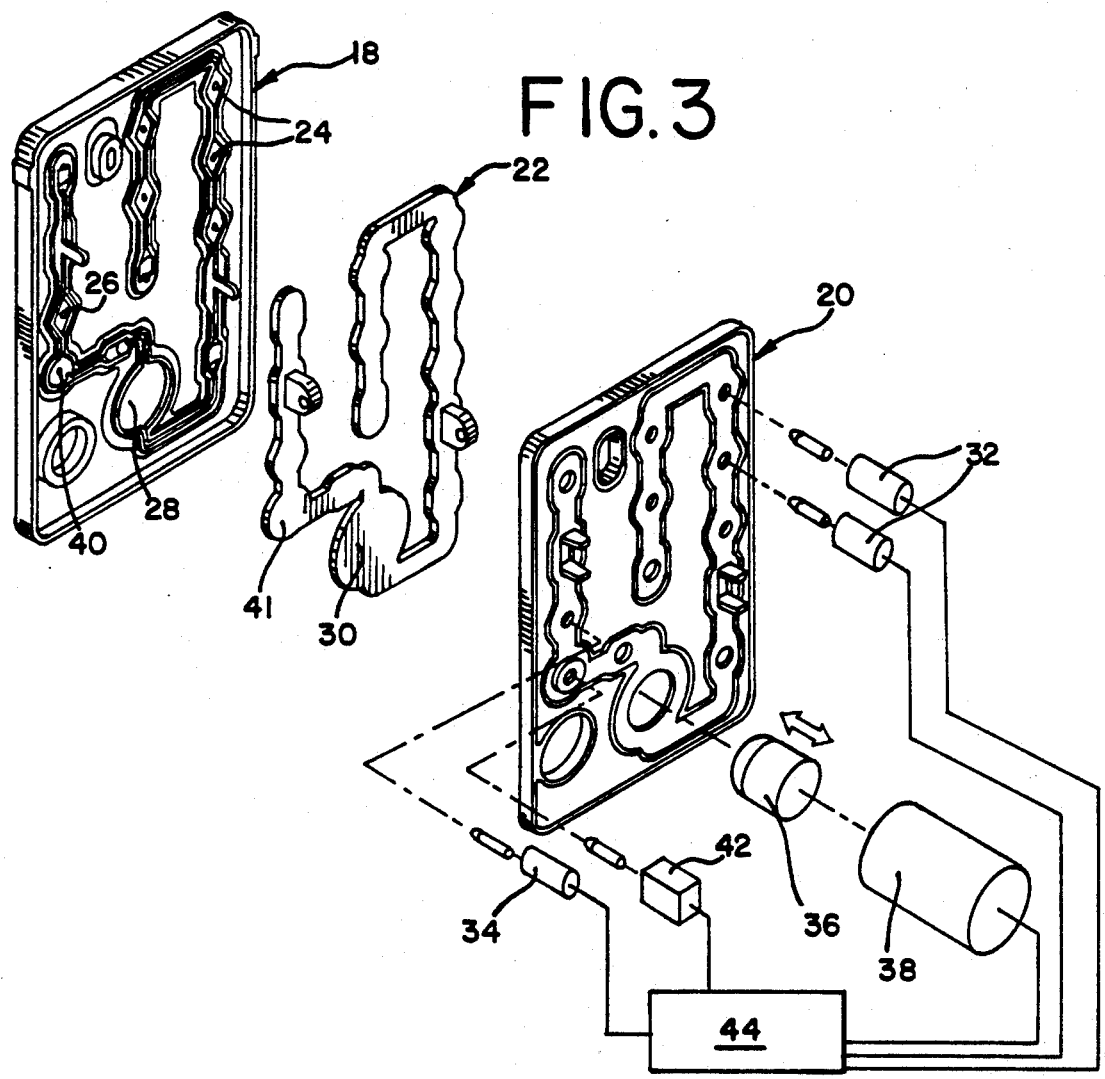
FIG. 3 is a diagrammatic, exploded perspective view illustrating the construction of the pump cassette shown in FIG. 2, and the manner in which components of the associated pump driver cooperate with the pump cassette.
Figure 4:
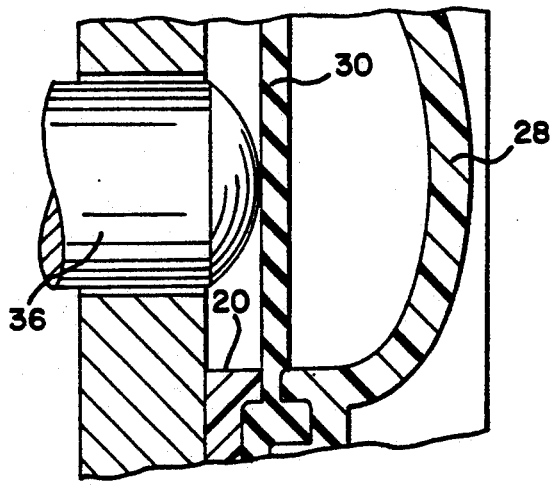
FIG. 4 is a fragmentary cross-sectional view illustrating a pump chamber of the pump cassette of the present system.

U.S. patent application Ser. No. 07/444,459, filed Dec. 1, 1989, now U.S. Pat. No. 5,062,774, hereby incorporated by reference, discloses in greater detail features of the illustrated solution pumping system. The disposable pump cassette 12 of the system, as particularly illustrated in FIGS. 2 and 3, includes a cassette body comprising juxtaposed front and rear body members 18 and 20, and a membrane-like elastomeric diaphragm 22 positioned in sandwich-like relationship between the front and rear cassette members.

The front and rear cassette members are joined to each other, such as by ultrasonic welding, such that the rear cassette member holds the elastomeric diaphragm 22 in tightly conforming relationship with the front cassette member 18. In this way, the diaphragm and the front cassette member together define a liquid flow path through which liquid flows within the cassette.

The cassette includes at least one, and preferably a plurality, of liquid inlets 24 which are configured to be joined via suitable tubing to containers of the various solutions to be compounded. The cassette further includes at least one liquid outlet 26 which is connected by suitable tubing to the container which receives the solution admixture being prepared.

Pumping of liquid through the cassette is effected by a self-contained positive displacement pump of the assembly. In particular, the front cassette member 18 includes a bowl-like pump chamber 28, with the diaphragm 22 including a pump portion 30 positioned adjacent to the pump chamber 28.

Control of liquid flow through the cassette is effected by a plurality of solenoid-operated valve actuators of the pump driver 14. The valve actuators are operable through openings defined by the rear cassette member 20, with the actuators acting against respective portions of the diaphragm 22 to cooperate in a valve-like manner with valve seats defined by the front cassette member 18. Thus, each of the various liquid inlets 24 is controlled by a respective valve actuator 32, with the liquid outlet 26 similarly controlled by a respective valve actuator 34.

Operation of the positive displacement pump of the cassette is effected by a reciprocable pump piston or plunger 36 of the pump driver 14. Operation of the pump is in accordance with above-referenced U.S. Pat. No. 4,639,245, to Pastrone et al. Essentially, liquid flow is effected by reciprocation of the pump piston 36 in timed relation to operation of inlet and outlet actuators 32 and 34. A reversible stepping motor 38, acting through a suitable threaded connection, provides reciprocable stroking of the pump piston for alternately deforming and relaxing the pump portion 30 of the diaphragm 22, thus effecting positive displacement of liquid in the pump chamber 28. During the advancing stroke of the pump piston 36, the diaphragm portion 30 is displaced into the pump chamber, with outlet 26 being opened by appropriate operation of its actuator 34. Liquid displacement on the order of 0.76 ml is typical in a current embodiment. During the return stroke of the pump piston, the outlet is closed, and an appropriate one of the inlets 24 is opened by operation of its respective actuator 32. During the return stroke, the resilient pump portion 30 of the diaphragm creates a negative pressure within the pump chamber, thus refilling the chamber with liquid for completing the pump cycle.

In order to monitor liquid pressures created within the pump cassette by the positive displacement pump, the present system preferably includes a pressure sensor 34 incorporated into pump driver 14. Front cassette member 18 defines a pressure chamber 40, with the diaphragm 22 including a portion 41 adjacent the pressure chamber, which portion 41 is engaged by a probe-like portion of the pressure sensor 42. The pressure sensor 42 is operatively connected with automated, programmable controls 44 of the present system. The controls 44 are preferably integrated into the pump driver 14, with the controls operatively connected with the various valve actuators, stepper motor 38, and other sensors of the system for effecting integrated operation thereof, including monitoring and analyzing occlusions in the system, as contemplated by the present invention.

Operation of the illustrated system is preferably effected in a manner which acts to minimize peak pumping pressures within the cassette 12, while maximizing liquid output of the device. In essence, this is achieved by operating the pump piston 36, and thus the positive displacement pump of the cassette, in a manner which creates a "square" pressure waveform. While the waveform is not truly "square", a practical impossibility, it is contemplated that during each pumping cycle, the system pressure is rapidly increased to the desired maximum, held at that desired limit until liquid from pump chamber 28 is displaced, and thereafter effecting refilling of the pump chamber as quickly as possible for the subsequent pump cycle. This is achieved by selectively varying the velocity of the pump piston during each advancing stroke, and preferably also during the return stroke.

Figure 5:
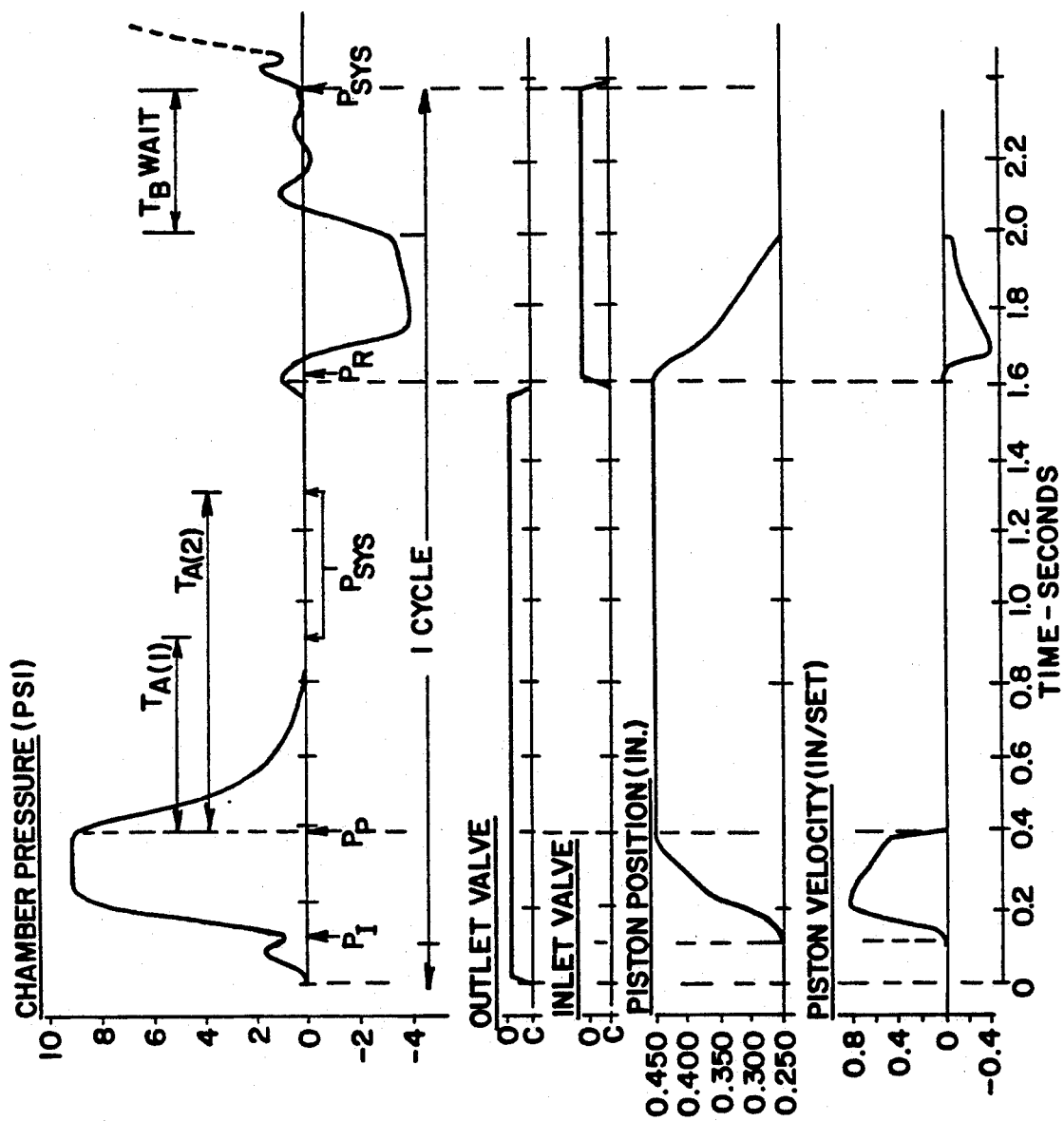
FIG. 5 illustrates a series of timing diagrams illustrating the operation of the pumping system in accordance with the present method during a pump cycle.

FIG. 5 illustrates timing diagrams associated with a single pump cycle, i.e., one advancing stroke and return stroke of the pump piston 36 acting in cooperation with the pump portion 30 of the diaphragm 32.

Figure 6:
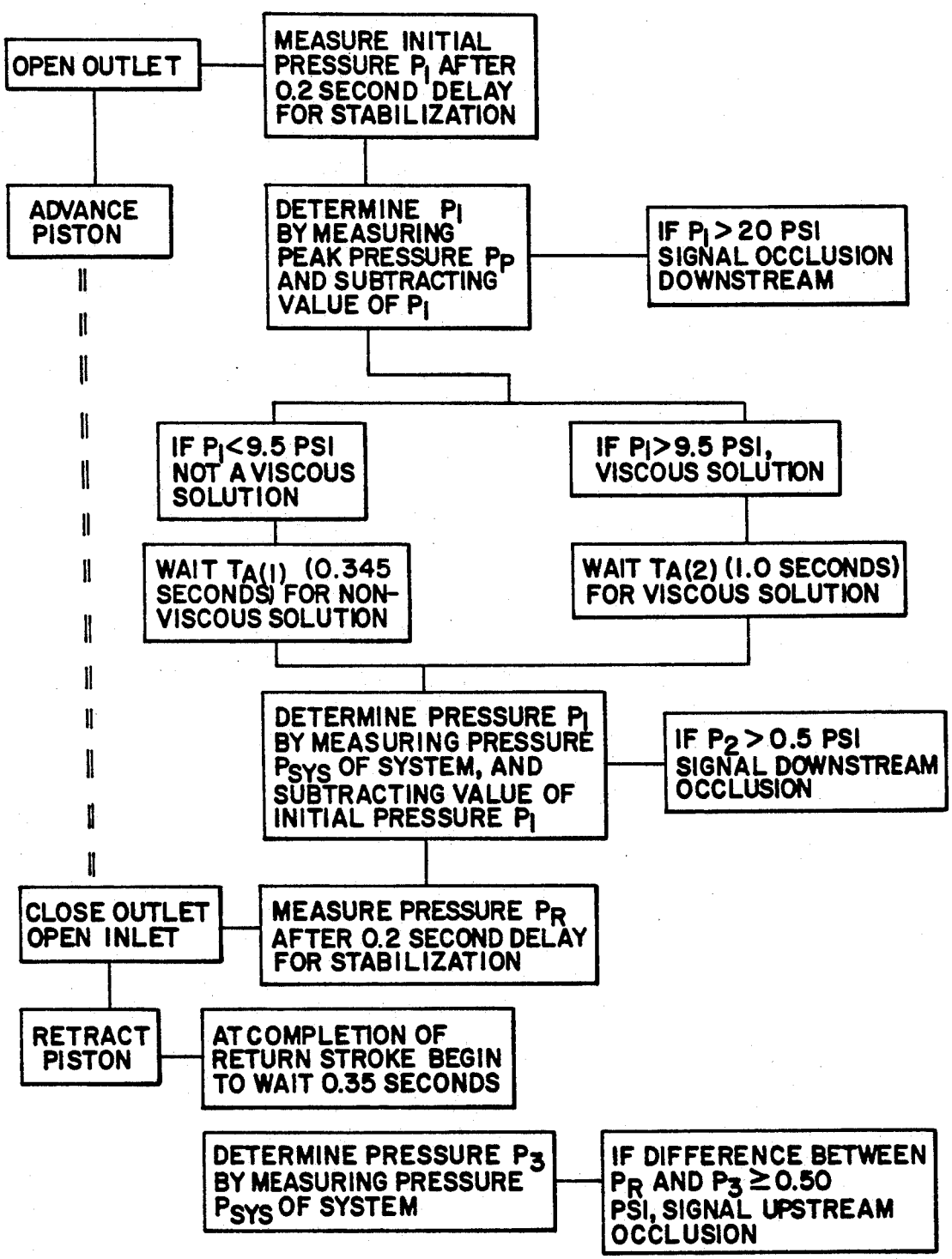
FIG. 6 is a flow diagram illustrating the sequence of steps of the present method.

FIG. 5 further illustrates the points during the pumping cycle at which pressures within the pumping system are monitored and analyzed, in accordance with the flowchart of FIG. 6. In accordance with the present method, pressures within the system at the pump chamber 28 are monitored (such as by pressure sensor 42), and thereafter analyzed to ascertain the existence of any occlusions or blockages in the system. It is presently preferred that a system operated in accordance with the present invention be controlled such that occlusion monitoring takes place on every pump cycle. In contrast, it is presently preferred that the sequence of steps for monitoring reference pressures, referred to hereinafter as $P_{REF}$ and $P_R$, be performed concurrently with the introduction of a new solution into the system. For example, when a system such as illustrated is used for preparation of parenteral solutions, the steps for obtaining reference pressures can be performed each time the system is operated to pump a new drug or other solution through the system, with the occlusion monitoring steps and analysis preferably taking place during each pumping cycle.

As will be appreciated, many different analysis techniques can be employed for monitoring and analyzing occlusions in a pumping system in accordance with the present invention. Because the system includes an arrangement which permits constant monitoring of system pressures, the pressure data thus generated can be analyzed and evaluated by any of a variety of techniques, such as Fourier transformation analysis, or other such date evaluation techniques. While the present disclosure contemplates an analysis technique which is desirably straightforward, reliable, and consistent, it is within the purview of the present invention to employ alternative analysis methods.

With reference to FIGS. 5 and 6, an initial pressure, $P_I$, is measured shortly after opening of an outlet valve (such as at outlet 26) of the system. Because opening and closing of the various outlet valves of the illustrated system introduce slight pressure fluctuations and instabilities into the system, measurement of $P_I$ is delayed a brief period of time (such as on the order of 0.2 seconds), after opening of the outlet valve (operation of the various valves typically introduces minor pressure fluctuations into the system). Pressure instabilities of the system are thus minimized before this initial pressure measurement.

As illustrated in the timing diagrams, initiation of movement of pump piston 36 initiates pumping of liquid in the system as liquid is positively displaced from the pump chamber 28 by the pump portion 30 of the diaphragm. As the system is operated to pump liquid, a measurement is taken of the peak pressure, $P_P$, at the pump during the pumping stroke. Thereafter, a pressure $P_1$, corresponding to the peak pressure of the system, is determined by subtracting $P_I$ from $P_P$.

As noted in the flowchart of FIG. 6, an initial occlusion check is made at this time by comparing the pressure $P_1$ to a predetermined value, $P_{OCC}$, thus providing an initial indication of any downstream occlusion. In the event that $P_1$ exceeds $P_{OCC}$ (which in a current embodiment is assigned a value of 20 psi), the system operates to provide a signal indicating occlusion of the system downstream of the pump.

The system is next operated, preferably during each pump cycle, to determine the viscosity characteristics of the solution being pumped. As will be appreciated, liquids which are less viscous ordinarily do not create pressures within the system which are as great as those created during pumping of a relatively viscous liquid. Additionally, the normal pressure fluctuations within the system are ordinarily less pronounced, and more quickly stabilized, when pumping of a relatively non-viscous liquid.

Accordingly, the system is next operated to compare the value $P_1$ to a predetermined value $P_{REF}$. $P_{REF}$ corresponds to a value selected to distinguish a viscous solution from a non-viscous solution; a value corresponding to 9.5 psi is employed in the current embodiment.

Depending upon the comparison of $P_1$ to $P_{REF}$, a time delay $T_A$ having one of two different values is provided. Specifically, the system is operating by waiting one of: (1) a first predetermined time interval $T_{A(1)}$ after determining if pressure $P_1$ is less than $P_{REF}$ (indicating a relatively non-viscous liquid), and (2) a second predetermined time interval $T_{A(2)}$, greater than $T_{A(1)}$, if the pressure $P_1$ is greater than $P_{REF}$ (indicating a relatively viscous liquid). In a current system, the relatively shorter time period, $T_{A(1)}$, corresponding to detection of a non-viscous solution, is provided at 0.345 seconds. In contrast, time interval $T_{A(2)}$, indicating a viscous solution, is 1.0 seconds, with this longer time interval permitting pressure stabilization of the relatively viscous liquid.

The provision of a time interval for system pressure stabilization is particularly important because of the compliant nature of the illustrated pumping system. The various components of the system, including the pump cassette and its elastomeric diaphragm, the tubing elements, the system seals, and the like, exhibit compliance, or flexing, in response to system pressurization. Such compliance can complicate pressure monitoring, since the resilient nature of these components results in cyclically undulating pressure instabilities within the system. These instabilities subside and decay over time, and become negligible.

At the conclusion of the selected time interval $T_{A(1)}$ or $T_{A(2)}$, a pressure $P_2$, corresponding to the pressure of the system, is determined. $P_2$ is determined by measuring the pressure of the system, $P_{SYS}$, and subtracting therefrom the value of the initial pressure $P_I$ of the system.

In the event that $P_2$ exceeds a predetermined value (0.5 psi in a current embodiment), the system is operated to provide a signal, such as an alarm or the like, indicating occlusion of the system downstream of the positive displacement pump. As will be recognized, a partial occlusion of the system can be detected in this manner, even though the occlusion may have not been sufficient to trigger the earlier, initial downstream occlusion detection step.

Occlusions upstream of the system pump are detected in a similar manner, that is, by effecting refilling of the pump chamber 28, and after a suitable time delay, comparing the system pressure with a predetermined value. Specifically, after opening of an inlet valve of the system (such as by operation of one of the valve actuators 32 to open one of the inlets 24), a pressure $P_R$ is measured. Again, it is preferred that a brief time period, on the order of 0.2 seconds in a current embodiment, be provided after opening of the inlet to permit pressure stabilization before measurement of $P_R$.

The controls of the system next establish completion of the return stroke of the pump, which can be established by monitoring the position of the pump piston 36 from the stepper motor 38. Since the pump piston is operated to remain in engagement with diaphragm portion 30, position of the pump piston accurately reflects the condition of the pump and the position of the diaphragm.

At completion of the return stroke of the pump, the system is operated to thereafter wait another predetermined time interval, $T_B$. Again, pressure stabilization is achieved during this waiting period. In a current embodiment, $T_B$ of 0.35 seconds is provided.

A pressure $P_3$ corresponding to the pressure $P_{SYS}$ of the system, is next determined, and a signal indicating upstream occlusion is provided in the event that the value of $P_3$ exceeds a predetermined value. This is preferably achieved by comparing the value of $P_3$ to $P_R$, with a signal provided indicating upstream occlusion of the system if the difference between $P_R$ and $P_3$ is greater than or equal to a predetermined value. In the current embodiment, a predetermined value of 0.50 psi has been employed. Again, occlusion of the system upstream of the positive displacement pump will result in the difference between $P_3$ and $P_R$ exceeding the predetermined value.

From the foregoing, it will be observed that numerous modifications and variations can be effected without departing from the true spirit and scope of the novel concept of the present invention. It is to be understood that no limitation with respect to the specific embodiment is intended or should be inferred. The disclosure is intended to cover, by the appended claims, all such modifications as fall within the scope of the claims.

What is claimed is:

1. A method of operating a solution pumping system including pump means which creates a positive liquid pressure at said pump means during a pumping stroke, and a negative liquid pressure at said pump means during a return stroke, said method comprising the steps of:

determining a pressure $P_1$ during a pumping stroke of said pump means corresponding to a peak pressure of said system;

waiting a predetermined time interval $T_A$ after determination of said pressure $P_1$;

determining a pressure $P_2$ corresponding to the pressure of said system; and providing a signal indicating occlusion of said system downstream of said pump means if $P_2$ exceeds a predetermined value.

2. A method of operating a pumping system in accordance with claim 1, including:

waiting a predetermined time interval $T_B$ after completion of said one of said return strokes;

determining a pressure $P_3$ corresponding to the pressure of said system; and providing a signal indicating occlusion of said system upstream of said pump means if the value of $P_3$ is equal to or greater than a predetermined value.

3. A method in accordance with claim 1, including:

determining an initial pressure $P_I$ prior to operation of said pump means, and determining said pressure $P_2$ by measuring a pressure $P_{SYS}$ of said system, and subtracting therefrom the value of the initial pressure $P_I$ of the system.

4. A method in accordance with claim 1, including:

comparing said pressure $P_1$ to a predetermined value $P_{REF}$.

5. A method in accordance with claim 4, wherein the waiting step comprises waiting one of: (1) a first predetermined time interval $T_{A(1)}$ after determining said pressure $P_1$ if said pressure $P_1$ is less than $P_{REF}$, indicating a relatively non-viscous liquid, and (2) a second predetermined time interval $T_{A(2)}$, greater than $T_{A(1)}$, if said pressure $P_I$ is greater than $P_{REF}$, including a relatively viscous liquid.

6. A method in accordance with claim 1, including comparing said pressure $P_1$ to a predetermined value $P_{OCC}$, and providing a signal indicating occlusion of said system downstream of said pump means if $P_1$ exceeds $P_{OCC}$.

7. A method of operating a solution pumping system including pump means which creates a positive liquid pressure at said pump means during a pumping stroke, and negative liquid pressure at said pump means during a return stroke, said method comprising the steps of:

measuring an initial pressure $P_I$ prior to operation of said pump means;

measuring a peak pressure $P_P$ during a pumping stroke of said pump means;

determining a pressure $P_1$, corresponding to a peak pressure of said system, by subtracting $P_I$ from $P_P$;

comparing pressure $P_1$ to a predetermined value $P_{REF}$;

waiting one of: (1) a first predetermined time interval $T_{A(1)}$ after determining if said pressure $P_1$ is less than $P_{REF}$, indicating a relatively non-viscous liquid, and (2) a second predetermined time interval $T_{A(2)}$, greater than $T_{A(1)}$, if said pressure $P_1$ is greater than $P_{REF}$, indicating a relatively viscous liquid;

determining a pressure $P_2$ corresponding to the pressure of said system by measuring a pressure $P_{SYS}$ of the system and subtracting therefrom the value of the initial pressure $P_I$ of the system; and providing a signal indicating occlusion of said system downstream of said pump means if $P_2$ exceeds a predetermined value.

8. A method in accordance with claim 7, including:

comparing said pressure $P_1$ to a predetermined value $P_{OCC}$, and providing a signal indicating occlusion of said system downstream of said pump means if $P_1$ exceeds $P_{OCC}$.

9. A method in accordance with claim 7, including:

measuring a pressure $P_R$ after said waiting step;

establishing completion of one of the return strokes of said pump means;

waiting a predetermined time interval $T_B$ after completion of said one of said return strokes;

determining a pressure $P_3$ corresponding to the pressure of the system, and comparing $P_3$ to $P_R$; and providing a signal indicating occlusion of said system upstream of said pump means if the difference between $P_R$ and $P_3$ is equal to or greater than a predetermined value.

10. A method of operating a pumping system including pump means which creates a positive liquid pressure at the pump means, comprising the steps of:

monitoring liquid pressure within said pumping system;

analyzing the monitored pressure within said system to identify an occlusion in said system; and providing a signal indicating occlusion of system, wherein said monitoring and analyzing steps include determining a pressure $P_1$ corresponding to a peak pressure of said system, waiting a predetermined time interval $T_A$ after determination of said pressure $P_1$, and determining a pressure $P_2$ corresponding to the pressure of the system, said step of providing a signal including providing a signal indicating occlusion of system downstream of said pump means if $P_2$ exceeds a predetermined value.

11. A method of operating a pumping system including pump means which creates a positive liquid pressure at the pump means, comprising the steps of:

monitoring liquid pressure within said pumping system;

analyzing the monitored pressure within said system to identify an occlusion in said system; and providing a signal indicating occlusion of system, wherein said pump means is operated to create a negative pressure in said system, said pump means is operated to create a negative pressure in said system, said monitoring and analyzing steps include measuring a pressure $P_R$ prior to operating said pump to create said negative pressure, waiting a predetermined time interval $T_B$ after operation of said pump to create said negative pressure, and determining a pressure $P_3$ corresponding to the pressure of the system, and comparing $P_3$ to $P_R$, said step of providing a signal including providing a signal including occlusion of said system upstream of said pump means if the difference between $P_R$ and $P_3$ is equal to or greater than a predetermined value.

12. A method of operating a pumping system including pump means which creates a positive liquid pressure at the pump means, comprising the steps of:

monitoring liquid pressure within said pumping system;

analyzing the monitored pressure within said system to identify an occlusion in said system; and providing a signal indicating occlusion of system, wherein said monitoring and analyzing steps include determining a pressure $P_1$ corresponding to a peak pressure of said system, and comparing said pressure $P_1$ to a predetermined value $P_{REF}$ to determine the viscosity of liquid being pumped by said system.

* * * * *